(12) United States Patent
Walker (10) Patent No.: US 6,183,437 B1
(45) Date of Patent: Feb. 6, 2001

(54) ELECTRONIC CONTROL UNIT AND TUBING ASSEMBLY SYSTEM FOR AUTOMATICALLY CONTROLLING URINARY IRRIGATION

(76) Inventor: Frank J. Walker, 403 Lily Flagg Rd. SE., Huntsville, AL (US) 35802

( * ) Notice: Under 35 U.S.C. 154(b), the term of this patent shall be extended for 0 days.

(21) Appl. No.: 08/969,396

(22) Filed: Nov. 13, 1997

Related U.S. Application Data (63) Continuation-in-part of application No. 08/500,473, filed on Jul. 10, 1995, now Pat. No. 5,688,239.

(51) Int. Cl.⁷ ............................. A61M 29/00; A61M 1/00
(52) U.S. Cl. ................. 604/96.01; 604/27; 604/102.02
(58) Field of Search ............................... 604/96, 102, 19, 604/27, 30, 34, 65, 67, 80, 101, 118, 131, 132, 246, 250, 257, 258, 262

(56) References Cited

U.S. PATENT DOCUMENTS

| | | |
|---|---|---|
| 3,902,492 | 9/1975 | Greenhalgh . |
| 4,211,233 | 7/1980 | Lin . |
| 4,262,668 | 4/1981 | Schmidt . |
| 4,579,554 | 4/1986 | Glassman . |
| 4,762,518 * | 8/1988 | Kreinick .............................. 604/245 |
| 5,007,897 | 4/1991 | Kalb et al. . |
| 5,306,241 | 4/1994 | Samples . |
| 5,720,721 * | 2/1998 | Dumas et al. .......................... 604/67 |

FOREIGN PATENT DOCUMENTS

| | | |
|---|---|---|
| 3306342 | 2/1983 | (DE) . |
| 449472 | 3/1991 | (EP) . |
| 2169206 | 1/1985 | (GB) . |
| 8811183 | 2/1988 | (WO) . |
| 8903232 | 4/1989 | (WO) . |
| 9304727 | 3/1992 | (WO) . |
| 9218199 | 10/1992 | (WO) . |

\* cited by examiner

*Primary Examiner*—Sharon Kennedy
*Assistant Examiner*—Ann Y. Lam
(74) *Attorney, Agent, or Firm*—Lanier Ford Shaver & Payne; Gerald M. Walsh; Frank M. Caprio (57) ABSTRACT

An electronic control unit and tubing assembly system for automatically controlling urinary irrigation is provided, including a tubing assembly and two embodiments of an electronic control unit. The tubing assembly includes tubing to connect to an irrigant supply source feeding a supply line, to a urinary catheter, and to a vent line connected to a fluid sensor assembly. The vent line is arranged so that irrigant flows into the vent line should the catheter drain become obstructed or should the supply line become kinked, and actuates a fluid sensor. An electronic control unit is in communication with the fluid sensor, and generates a control circuit that is responsive to the fluid sensor. When the fluid sensor detects a catheter obstruction, the circuit changes states and closes a pinch valve to shut off the flow of irrigant. In this manner, the system prevents the patient from suffering bladder distension, perforation, or rupture due to a "runaway" urinary catheter. The first embodiment of the electronic control unit automatically resumes the flow of irrigant once the obstruction or kink is cleared, with or without human intervention. The second embodiment provides an electromechanical device that must be manually cocked to initiate irrigant flow, that is shut by a mechanical trigger should an obstruction occur, and that must be manually re-cocked to resume irrigant flow.

32 Claims, 6 Drawing Sheets

ELECTRONIC CONTROL UNIT AND TUBING ASSEMBLY SYSTEM FOR AUTOMATICALLY CONTROLLING URINARY IRRIGATION

This application is a Continuation In Part (CIP) of U.S. application Ser. No. 08/500,473, filed July 10, 1995, now U.S. Pat. No. 5,688,239.

BACKGROUND

Urological irrigation is a very common medical procedure and is initiated whenever irrigation is indicated following bladder surgery or bladder trauma, as well as for gross hematuria of indeterminate etiology for both female and male patients. In addition, it is routinely used following TURPS (Transurethral Resection, Prostate), one of the most common of male surgeries, with over 220,000 such operations performed annually in the United States alone.

Historically, irrigation for all of these procedures is by CBI (Constant Bladder Irrigation) using an indwelling irrigating catheter commonly referred to as a Foley "3-way catheter". The "Foley" designation refers to a catheter that employs a balloon inflated by the introduction of sterile water through a valve, known as a Luer lock, into the balloon after the catheter is inserted into the patient's bladder. The purpose of the Foley inflatable balloon is to retain the catheter within the bladder to prevent inadvertent removal of the catheter.

The "3-way" designation refers to the three lumens employed in the catheter's construction. Those three lumens function as follows: (1) balloon inflating/deflating lumen; (2) bladder irrigation lumen; and (3) bladder drain lumen. Generally, the flow rate of the irrigating fluid is manually adjusted by the nursing personnel and the irrigant is constantly dripped into the bladder until completion of the treatment.

Unfortunately, from the patient's perspective, there are distinct and potentially serious problems with this seemingly simple procedure. As an example, the typical TURP patient is fitted with a "3-way" indwelling catheter and is given CBI (Constant Bladder Irrigation) generally for a 24 hour period, during which time he would consume approximately 20 3-liter bags of saline irrigant while recuperating in his room. An empty, normal bladder has a volume of about 500 cc. Typically, irrigant is fed into the bladder as an approximate flow rate of 2500 cc/hour. If the bladder drain lumen becomes clogged, given the bladder volume and the flow rate, the bladder would become fully distended in approximately 10 to 12 minutes. Catheter drain lumens routinely become clogged or blocked which is a rather common problem with this type of surgery as a result of blood clots and/or surgical debris. Thus, there is a real risk of injury to the patient should his catheter's drain lumen become clogged.

If the drain lumen is not cleared within that 10–12 minute window, the patient's bladder could be over-distended or perforated. Full bladder distention is not only extremely uncomfortable for the patient, but is also a potentially dangerous condition that can readily lead to bladder perforation or rupture, if not immediately rectified. This problem imposes a risk of serious liability on the hospital. Thus, hospitals frequently assign a full time nurse to monitor closely those patients who demonstrate a propensity for this condition.

Bladder distention is particularly serious for patients recovering from bladder surgery, such as bladder cancer, wherein the bladder wall tissue is locally thin and weak in the resected areas. Under such conditions, every effort must be made to prevent bladder distention. Once again, hospitals commonly assign a full time nurse to such patients to avoid bladder distention. Unfortunately, assigning full-time nurses to such patients drastically increases hospital labor costs. In today's "managed care" environment, hospitals are typically reimbursed a fixed amount for each patient recovering from a specific surgical procedure, regardless of their length of hospital confinement or the extent of nursing care required. Therefore, hospitals must save labor costs whenever possible.

Accordingly, there is a need in the art for a system that constantly monitors the status of a catheter and a catheter drain lumen, and automatically interrupts the flow of irrigant should the drain lumen become kinked or obstructed, or should the supply lumen become kinked. To save on labor costs, such a system should also automatically resume the flow of irrigant should the drain lumen become unkinked or cleared on its own.

Another important consideration for hospitals is the quantity of irrigant consumed during post-operative treatment with traditional CBI methods. As noted above, a typical CBI patient will consume about 60 liters of saline irrigant per 24 hour recovery period. Clearly, the cost of such quantities of irrigant can be considerable. Accordingly, a need exists for a device and method that minimizes the amount of irrigant used during post-operative treatment of patients requiring urological irrigation.

SUMMARY

The above needs in the art motivated the instant invention. Accordingly, a first objective of this invention is to provide a device for constantly monitoring the status of the drain lumen of a catheter, and for automatically interrupting the flow of irrigant should the drain lumen become obstructed.

A second objective is to provide a device for automatically resuming the flow of irrigant should the drain lumen obstruction clear itself with or without human intervention.

A third objective is to provide a device that flushes the patient with irrigant, while minimizing the amount of saline irrigant used.

A fourth objective is to provide a device including an electronic control unit and a tubing assembly, with the electronic control unit communicating with the tubing assembly to monitor the status of the drain lumen and to interrupt the flow of irrigant should the drain lumen become obstructed.

A fifth objective is to provide an electronic control unit including a pinch valve whose operation is governed by a control signal, and wherein the control signal is manipulated by the tubing assembly.

A sixth objective is to provide a tubing assembly including a vent line being in communication with an irrigant supply line, and a fluid sensor being in communication with the vent line so that the fluid sensor detects irrigant in the vent line.

A seventh objective is to provide a tubing assembly including a fluid sensor for manipulating a control signal generated by the electronic control unit.

An eighth objective is to provide an electronic control unit that allows the user to select from a plurality of flushing modes.

A ninth objective is to provide a low-cost electronic control unit that is manually-operated, yet automatically detects urinary catheter obstructions and interrupts the flow of irrigant once an obstruction is detected.

A tenth objective is to provide an electronic control unit with the ability to adjust the volume of irrigant supplied to the urinary catheter.

DETAILED DESCRIPTION OF THE PREFERRED EMBODIMENT

The invention will now be described in detail with reference to the attached drawings.

Figures 1, 1A, 1B:
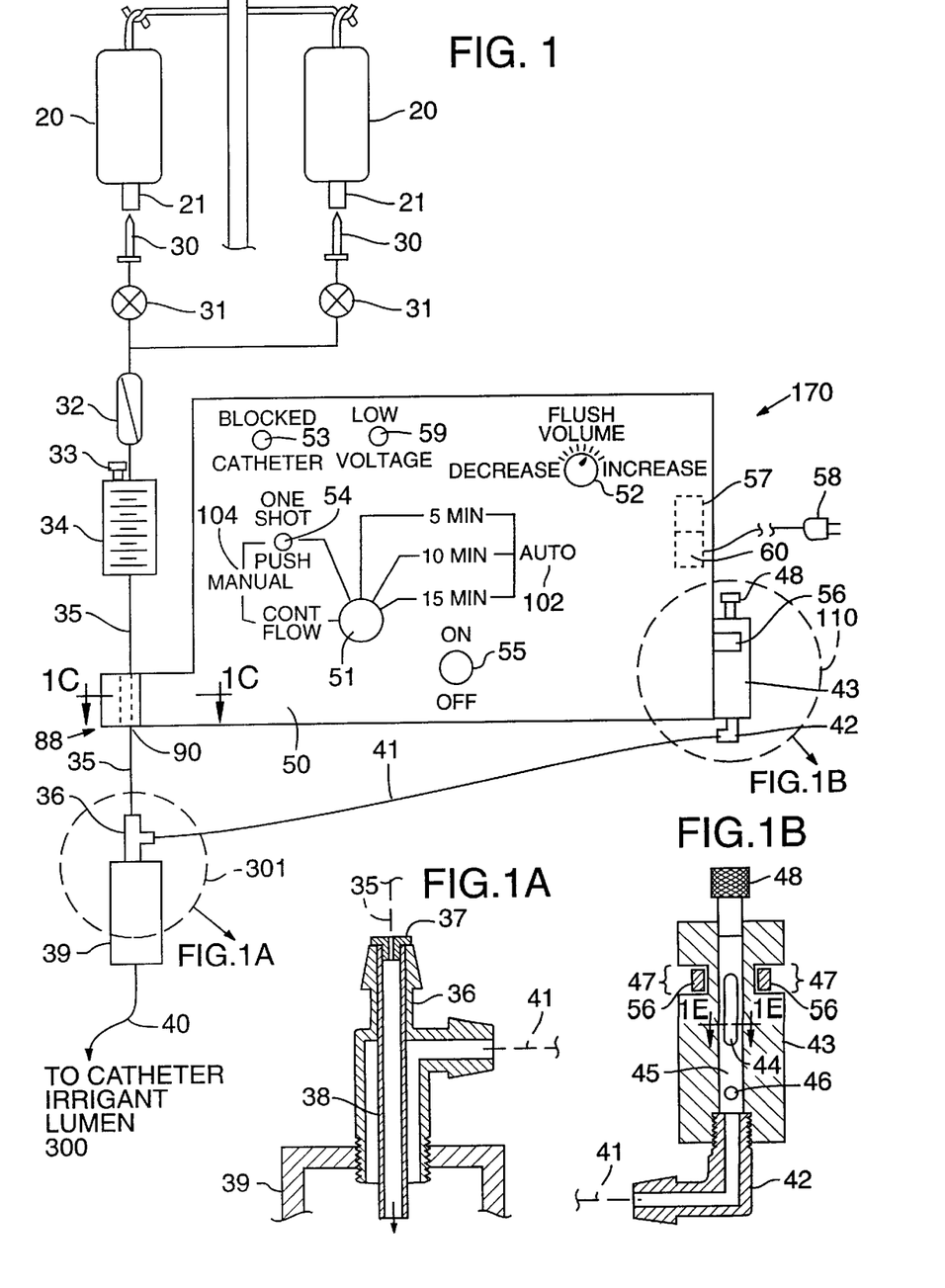
FIG. 1 is a schematic view in elevation of the tubing assembly and electronic control unit assembled with the irrigant supply components to form a complete catheterization system.
FIG. 1A is a fragmentary, detailed, sectional view of a combination flow-restrictor and bypass venting tee.
FIG. 1B is a fragmentary, detailed, sectional view of the obstructed catheter detector assembly.

FIG. 1 is a schematic diagram of the preferred embodiment of the invention, shown in its operating environment. One or more collapsible supply bags 20 containing irrigant are suspended from IV pole 10, and hollow spikes 30 are driven into outlets 21. Irrigant from supply bags 20 then flows under the force of gravity through on/off valves 31 and flow regulating clamp 32 into supply reservoir 34. Flow regulating clamp 32 is used to regulate the rate of flow of irrigant as it refills reservoir 34 between flushes. Supply reservoir 34 includes combination air vent/check valve 33, which is a hydrophobic filter that permits the passage of air but blocks fluid flow, thereby preventing "air lock" and permitting supply reservoir 34 to fill and empty quickly when pinch valve assembly 88 is opened. A section of thin-walled flexible tubing 35 connects supply reservoir 34 to tee 36, which is described in more detail below. Tubing 35 passes through pinch valve assembly 88 of electronic control unit 170, which is also described in more detail below.

Electronic control unit 170 includes pinch valve assembly 88, which selectively interrupts the flow of irrigant in tubing 35. Pinch valve assembly 88 is controlled by selector switch 51, by control knob 52 and by fluid sensor assembly 110.

Electronic control unit (ECU) 170 includes cabinet 50, which provides a housing for the electronic and mechanical components comprising electronic control unit 170. Cabinet 50 may be formed of any convenient rigid material and formed in any suitable shape. Electronic control unit 170 receives AC current through power cord 58. A suitable power supply 60 converts the AC current to the power level appropriate for the electronic components comprising ECU 170. The power supply feeds rechargeable battery 57, which offers distinct advantages when ECU 170 is used with ambulatory patients. When the patient is moved, the attendants need only unplug power cord 58, and ECU 170 will be powered by rechargeable battery 57, and will remain operational so long as battery 57 is charged.

ECU 170 preferably includes a power switch 55 controlling the overall operation of ECU 170, LED 53 indicating a blocked catheter, LED 59 indicating low battery voltage. Control knob 52 is preferably implemented with a potentiometer, and controls the volume of irrigant discharged during each flush cycle. Flush mode selector knob 51 allows the user to select from several flushing modes. A first mode is "continuous flow," which is similar to the constant bladder irrigation (CBI) methods described above. A second mode is "one-shot," which allows the user to press button 54 to manually release irrigant to the patient. The first and second modes are collectively labeled as 104. A third mode 102 is an automatic mode, which periodically releases a volume of irrigant according to a selected time schedule. The volume of irrigant is determined by the position of control knob 52. For example, FIG. 1 illustrates 5 minute, 10 minute, and 15 minute release intervals. It should be understood, however, that any number of intervals or any duration of interval is within the scope of the current invention. Also, various mechanical means could be substituted for the control knobs illustrated in FIG. 1, including push buttons, sliders, digital keypads and displays, or other equivalent selection devices.

Periodic flush irrigation materially reduces the consumption of irrigant as compared to CBI. Clinical trials to date have consistently demonstrated an approximate reduction of 85% in both the irrigant consumed as well as the attendant reduction in nursing care, again an important consideration with hospital "managed care".

Mounted to the side of ECU 170 is a means 56 for generating a control circuit. Generating means 56 is preferably a photon-coupled interrupter module including a photon emitter and a photon detector. Although photon energy is the operative medium in the preferred embodiment, it should be understood that other operative media, such as electrical current, electromagnetic fields, or other electrical or mechanical phenomena, could be suitable under certain circumstances. Generating means 56 is permanently and fixedly joined to ECU 170, and is designed to interface to fluid sensor assembly 110, which is described in further detail below.

FIG. 1A is a schematic diagram of some of the components of tee assembly 301. Tubing assembly 301 includes flexible tubing 35, fitting 36, flow restrictor 37, sump reservoir 39, rigid tubing 38, vent line 41, and irrigant supply line 40. Irrigant flows through flexible tubing 35, flow restrictor 37, and rigid tubing 38 into sump reservoir 39. The irrigant then flows from sump reservoir 39 into irrigant supply line 40, and then on to catheter 300 (not shown). So long as catheter 300 functions normally, vent line 41 does not come into play.

However, if irrigant supply line 40 is kinked, or if the drain lumen of catheter 300 becomes obstructed with blood clots or surgical debris, the incoming irrigant fills tubing 40 and sump reservoir 39. Fitting 36 is located at the entrance of sump reservoir 39 and thin wall tubing 35 attaches to fitting 36. A length of rigid, possibly stainless steel tubing 38 fits internally within fitting 36. Flow restrictor 37 is also installed in the upstream end of tubing 38 to restrict the fill rate of sump reservoir 39.

The downstream portion of tubing 38 is positioned in fitting 36 so as to permit unrestricted communication between reservoir 39 and vent line 41 by means of the annulus between tubing 38 and fitting 36. Irrigant flows through restrictor 37 into tubing 38, which terminates approximately an inch below the downstream end of fitting 36, thereby discharging the irrigant into sump reservoir 39. Since the downstream end of tube 38 is located well below the tee connection to vent line 41, the only time that irrigant would enter vent line 41 is when, and if, there was a blockage of any downstream portion of irrigant supply line 40 and/or catheter 300. Under those circumstances, irrigant would not flow freely into catheter 300, thereby backing up the irrigant past fitting 36 and into vent line 41 and thence into infrared sensor assembly 110.

Sump reservoir 39 temporarily stores irrigant when ECU 170 is operating in the flush mode and rapidly discharges a larger quantity of irrigant than catheter 300 can immediately dispose of. Were sump reservoir 39 not provided, irrigant might fill line 40 and flow into vent line 41, and cause fluid sensor assembly 110 to register a false-alarm. Sump reservoir 39 thus buffers the catheter and ECU 170, and prevents sensor assembly 110 from false-alarming.

This preferred embodiment of ECU 170 functions equally well with either a conventional 3-way catheter or the proprietary 4-way catheter as described in my U.S. application Ser. No. 08/500,473, filed Jul. 10, 1995, now U.S. Pat. No. 5,688,239, the entire disclosure of which application is herein incorporated by reference, and can be used whenever urinary tract irrigation is medically indicated.

There is provided a means of accumulating a measured amount of irrigant to be released periodically for flush-irrigating the desired urinary organ with a rush of irrigant, as well as providing constant urinary irrigation by means of either the 4-way or the 3-way catheter if medically indicated.

FIG. 1B is a schematic view of the components comprising fluid sensor assembly 110. Body 43 defines two locating slots 47, which receive generating means 56. As described above, generating means 56 is permanently joined to cabinet 50 of ECU 170. However, body 43 is detachably joined to cabinet 50 proximate generating means 56. The specific structure comprising this detachable fit is not illustrated in FIGS. 1 and 1B, since choosing suitable structure is within the level of skill in the art. Suitable structure might include hoop and loop fasteners, snap fasteners, or other releasable fasteners. Fluid sensor assembly 110, vent line 41, body 43, and tubing assembly 301 are preferably part of a pre-packaged, pre-sterilized tubing string.

It should be understood that the locations shown for generating means 56 are merely illustrative and are not limiting. Also, the exact devices comprising generating means 56 will vary, depending on which operative medium is chosen. In the preferred embodiment, photon energy is the operative medium, and generating means 56 is a photon emitter and photon detector combination, such as an NTE 3101 photon-coupled Interrupter module with Darlington output. Also, the specific shape of body 43 and locating slots 47 as shown in FIG. 1A are merely illustrative and are not limiting. Body 43 and locating slots 47 should be arranged according to the size, shape, location, and configuration of generating means 56. Thus, the shape and configuration of body 43 and locating slots 47 may vary depending on the specific devices chosen to implement generating means 56.

The preferred embodiment of body 43 defines an elongated chamber 45, which carries a manipulating means 44 along its length. If generating means 56 using the preferred embodiment of a photon emitter and a photon detector is used, then manipulating means 44 can be an opaque float that selectively interrupts the flow of photons from the emitter to the detector. Thus, an opaque float is the preferred means 44 for manipulating the control circuit generated by means 56 joined to ECU 170. However, it should be understood that the precise component chosen to implement manipulating means 44 will vary depending on the precise component chosen to implement generating means 56. Manipulating means 44 should interact with generating means 56 to manipulate the control circuit generated by means 56. Thus, FIG. 1B merely illustrates the preferred embodiment and is not meant to limit the invention.

Clearly, the control circuit can be implemented a number of different ways, such as defining a circuit having a normally-open first state, and transitioning to a closed second state that indicates a catheter obstruction. Alternatively, the circuit could be defined with a normally-closed first state, and transitioning to an open second state.

In the preferred embodiment, means 56 for generating a control circuit is a photon emitter and a photon detector defining a normally-closed circuit that is opened by an opaque float. However, depending upon the application, other components for generating a selectively interruptible control circuit may be suitable. Although the operative medium in the preferred embodiment is photon energy, other electrical media may suitable, such as electronic signals, electromagnetic fields, direct current connections, or digital signals. Also, mechanical devices such as microswitches or other mechanical switchgear may be suitable in some applications.

Manipulating means 44 should be chosen to interact with the control circuit generated by means 56. As stated above, means 56 can generate a control circuit having a number of configurations and using several different operative media. The choice of manipulating means 44 will vary depending on the choice of control circuit configuration and operative media. For example, if the control circuit is chosen as a normally-open circuit transitioning to a closed state when the catheter is obstructed, then manipulating means 44 should be chosen to make the control circuit when fluid sensor assembly 110 indicates that the catheter is obstructed.

Vent line 41 connects to body 43 via fitting 42, which may be L-shaped or any other convenient shape. Fitting 42 places vent line 41 in fluid communication with chamber 45. Thus, when irrigant flows into vent line 41 after catheter 300 becomes obstructed due to a kinked line or other blockage, the irrigant will eventually flow through fitting 42 into chamber 45.

In the preferred embodiment, body 43 is oriented so that chamber 45 is generally parallel to the force of gravity, such that gravity biases manipulating means 44 downward. Pin 46 is located toward the lower end of chamber 45, and interrupting means 44 normally rests against pin 46. Thus, pin 46 prevents interrupting means 44 from blocking or plugging fitting 42, and defeating the function of fluid sensor assembly 110. Chamber 45 is vented through hydrophobic filter 48, which permits air venting, but prevents the escape of irrigant.

As irrigant enters chamber 45, the irrigant will lift manipulating means 44 from pin 46, and will raise manipulating means 44 toward the top of chamber 45. When manipulating means 44 is toward the top of chamber 45, means 44 will manipulate the control circuit generated by means 56. In the preferred embodiment, generating means 56 includes a photon emitter and a photon detector, and fluid sensor assembly 110 will locate chamber 45 between the photon emitter and the photon detector. When catheter 300 is clear, and there is no irrigant in vent line 41, then manipulating means 44 will rest upon pin 46, held in place by gravity.

In its resting position, manipulating means 44 will have no effect on the control circuit generated by means 56. However, if catheter 300 becomes obstructed, and irrigant enters vent line 41, then the irrigant will raise manipulating means 44 into position between the two components comprising generating means 56. In this raised position, manipulating means 44 interferes with the control circuit generated by means 56, thus alerting ECU 170 to close pinch valve assembly 88 to interrupt the further flow of irrigant. In the preferred embodiment, manipulating means 44 is an opaque float that blocks the flow of photons from the emitter to the detector when the float is in the raised position, and allows photons to flow between the emitter and the detector when the float is no longer positioned between the emitter and the detector.

Figure 1C:
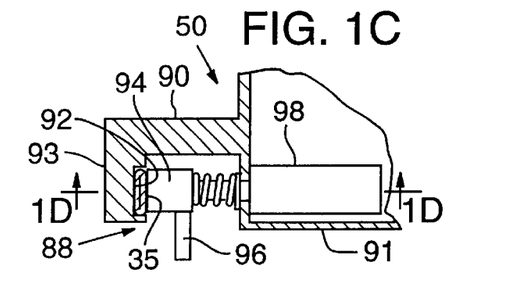
FIG. 1C is a fragmentary, detailed, sectional view of the valve means employed in the apparatus of FIG. 1, taken along line 1C—1C of FIG. 1.
Figure 1D:
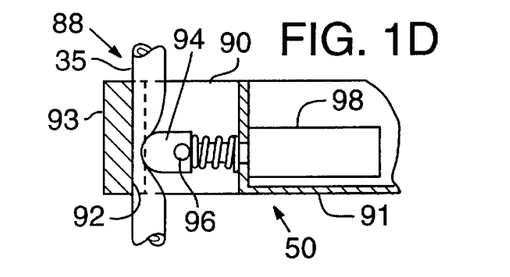
FIG. 1D is a detailed fragmentary, sectional view taken along line 1D—1D of FIG. 1C.
Figure 1E:
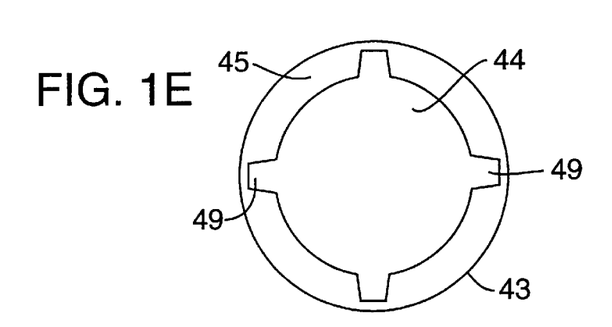
FIG. 1E is a detailed fragmentary, sectional view taken along line 1E—1E of FIG. 1B.

As depicted in FIG. 1E, manipulating means 44 may be provided with several thin raised knobs 49 that center manipulating means 44 within chamber 45 and that reduce the surface area contact between means 44 and the wall of chamber 45 of body 43. Knobs 49 thus prevent manipulating means 44 from adhering to the wall of chamber 45 by surface tension effect, and thus immobilizing manipulating means 44 and defeating the fluid detecting capability of fluid sensor assembly 110. Knobs 49 also center manipulating means 44 within cavity 45.

Pinch valve assembly 88 is illustrated in FIGS. 1, 1C and 1D.

The connecting conduit between reservoir 34 and sump reservoir 39 includes a length 35 of thin wall resilient tubing made of resilient plastic such as silicone or other suitable resilient material. Pinch valve assembly 88 is the preferred means for selectively interrupting the flow of irrigant within tubing length 35.

Interrupting means 88 includes lever 96 fixed to the head of ram 94. Ram 94 is operated by solenoid 98, which is in electrical communication with generating means 56. Bracket 90 is attached to cabinet 50, and is generally L-shaped. Bracket 90 includes anvil 93, which opposes ram 94. Anvil 93 further includes notch 92, into which tubing 35 fits. By pulling lever 96, ram 94 can be manually retracted to open the valve and allow irrigant to flow, but against the compression of its associated spring. Upon release of lever 96, the spring drives ram 94 and pinches tubing 35 against anvil 93 to close the valve and interrupt the flow of irrigant.

Interrupting means 88 includes an electrically operated "pull" solenoid 98, arranged as shown in FIGS. 1C and 1D to open the valve against the compression of the valve spring. The valve spring then returns the valve to its normally closed position upon de-energization of the solenoid, thereby shutting off the flow of irrigant.

Although FIGS. 1C and 1D illustrate a preferred embodiment of interrupting means 88, other devices may be suitable, so long as they are electrically operable to selectively interrupt the flow of irrigant. Examples of such devices might include servomotor-operated mechanical linkages, flow restrictors, water shut-off devices, or similar devices.

Figure 2:
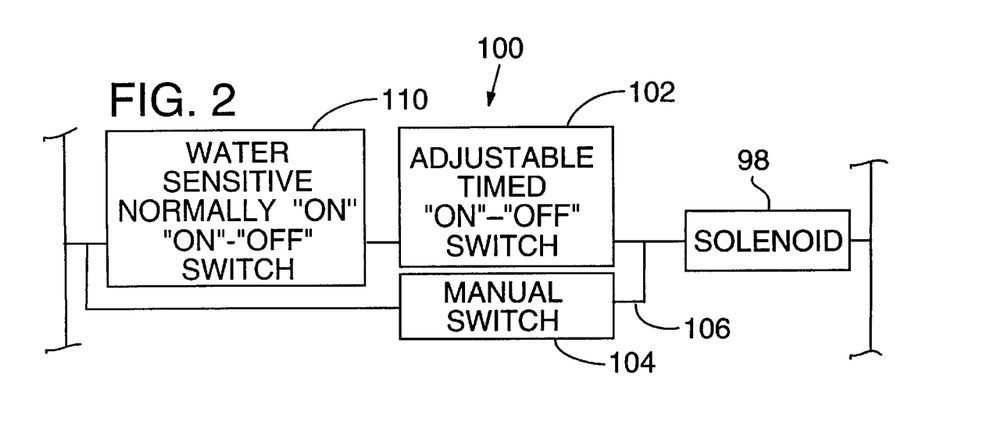
FIG. 2 is a schematic diagram of the electronic controls for the apparatus of FIG. 1.

FIG. 2 is a schematic diagram of the circuit controlling the operation of pinch valve assembly 88.

As therein depicted, the electric circuit 100 (preferably 12 VDC for patient safety), includes in series circuit relationship solenoid 98 and an adjustable, timed, on-off switch 102 for the operation of the same. If desired, in a shunt circuit 106 there may also be included a manual electronic switch 104. This serves the same purpose as lever arm 96 on spring compressed ram 94, in permitting a single operation of the valve when the ram is electrically actuated by push switch 54.

Electrical power for the device can either be AC, or DC, however, preferably it would be battery powered by a rechargeable battery 57, recharged by AC power cord 58. Accordingly, while the patient is in the operating room and/or recovery room, or ambulatory between the latter and the hospital room, battery 57 would power the device. After the patient is taken to the hospital room, power cord 58 would be used to recharge the battery and furnish power for the unit on an extended basis.

The volume of each flush is determined by the length of time that the pinch valve is held open with each "flush" command. Control knob 52, preferably implemented with a potentiometer, is used to vary the hold-open time as required to achieve the desired volume.

Following urinary tract surgery it frequently occurs that the patient's catheter becomes clogged with blood clots and/or surgical debris, or that the catheter drain conduit becomes kinked shutting off the flow. If either of these contingencies occurs, and if the supply of irrigating fluid is continued, pressure will build up in the urinary tract, resulting in severe and potentially dangerous patient discomfort, or in extreme cases even bladder perforation (rupture).

If this event occurs in the use of the presently described apparatus, the irrigant will back up in irrigant supply line 40 and sump reservoir 39 to enter vent line 41, which communicates with the normally open fluid sensor assembly 110. Upon electronically detecting this back-up of irrigant, fluid sensor assembly 110 closes the pinch valve assembly 88, thereby arresting the further flow of irrigant, simultaneously it turns on a flashing LED 53 and an audible buzzer (not depicted) to alert the patient and/or medical personnel that a catheter blockage has occurred. Upon clearing the blockage, with or without human intervention, the light and audible alarm turn off and the normal, selected periodic flow mode of the irrigant is restored automatically.

Figure 3:
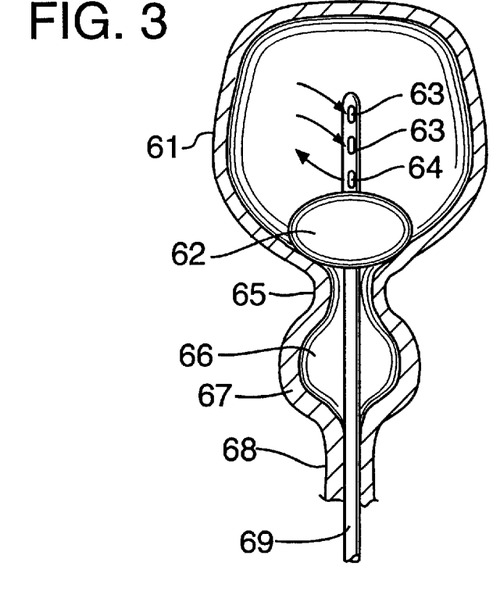
FIG. 3 is a schematic diagram of a portion of the male urinary tract with the conventional 3-way bladder irrigating and drain catheter in place.

FIG. 3 is a schematic view of the construction and manner of use of the "3-way" urinary catheter system currently routinely used in hospitals throughout the world to irrigate the bladder. As depicted in FIG. 3, the male urinary anatomy involved includes the urethra 68, the prostate 67, bladder neck 65 and the bladder 61. The subject "3-way" urinary catheter performs well when constant bladder irrigation is indicated, however, it does not provide means of irrigating the prostate when used following prostate surgery (TURP)

wherein the prostate is left with a central cavity 66 of surgically resected tissue. Accordingly, when prostate surgery is performed it is desirable to flush irrigate the prostate using the "4-way" urinary catheter as described in the parent patent application (U.S. Pat. No. 5,688,239).

When the conventional "3-way" urinary catheter is employed in the hospital experience described above, the catheter is comprised of an elongated tube 69 equipped with positioning means comprising a conventional fluid-inflated "Foley" balloon 62.

The proximal end of the catheter has one or more irrigation ports 64 connected to a source 20 of irrigation fluid. It also has one or more drain ports 63 which connect to a receiving receptacle for urine and spent irrigating fluid. It is clearly evident from the foregoing why the prostate cavity is inefficiently irrigated, if it is irrigated at all. The irrigating fluid was introduced into the bladder through port 64 and promptly exited through adjacent ports 63, completely bypassing the prostate and resected area 66.

It is to be noted that in the use of this style catheter, the bladder is placed in an imperfectly sealed relation to the prostate cavity by means of locating balloon 62. The only way for blood, urine and surgical debris to be removed from the prostate area is for it to leak past balloon 62 and exit via ports 63 in the bladder. Such leakage is minimal, however, due to the complete lack of any catheter irrigation and/or drainage facilities within the prostate, as well as because of the sealing action of the locating balloon.

In addition to largely inhibiting the flow of irrigation fluid from the bladder to the prostate area, the imperfect seal created by balloon 62 has another adverse effect. It permits urine from the bladder to leak into the surgically resected prostate and accumulate there without there being any provision for drainage until the catheter ultimately is removed.

It is true that small amounts of urine and other fluids which accumulate in the prostate can, under some circumstances, leak past the circumferential fit between the catheter and the urethra downstream from the prostate, particularly if the catheter is a loose fit. However, such amounts are not sufficient to irrigate the prostate. Additionally in practice, this leakage is discouraged. Quite often provision is made to seal against it, inasmuch as it results in patient discomfort and soiling of his bedding and/or clothing.

In any event, such leakage generally is not relied upon as a primary means of draining the prostate. For all practical purposes, the prostate does not have any provision for drainage when the 3-way catheter is in place. Most of the stale urine, blood products and debris is left to accumulate in the prostate cavity, where it is subject to biological degradation, until withdrawal of the catheter several days following surgery.

Figure 4:
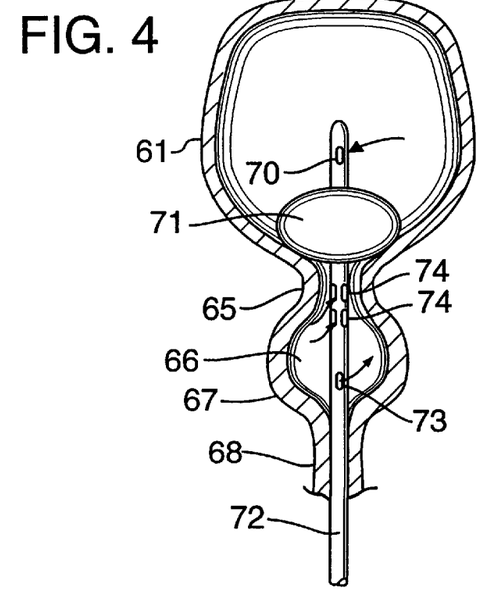
FIG. 4 is a schematic diagram of the male urinary tract similar to FIG. 3, but with the 4-way prostate irrigating catheter with separate drains for the prostate and bladder in place.

FIG. 4 is a schematic diagram of the proprietary four-way catheter which is designed to be used following prostate surgical (TURP) operations, and is fully described in U.S. application Ser. No. 08/500,473, filed Jul. 10, 1995, now U.S. Pat. No. 5,688,239. In four-way catheter 72, one or more urine drain ports 70 are provided at the proximal tip. These connect with a receiving receptacle at the other end of the catheter.

Also provided in the proximal portion of the catheter are one or more fluid dispensing ports 73 and one or more spent fluid drain ports 74 positioned within the resected prostate cavity 66 by means of positioning balloon 71. This balloon is similar in construction and purpose to Foley balloon 62 of FIG. 3, previously described.

Fluid dispensing ports 73 connect with a source 20 of irrigation fluid under hydrostatic pressure associated with valving means for delivering the fluid to the prostate area in measured amount at predetermined intervals, as will be described in detail hereinafter.

Balloon 71 assures the proper positioning of the catheter with all three sets of ports in their desired operative positions, i.e., with urine drain ports 70 in the bladder, and with both fluid dispensing port 73 and fluid drain ports 74 in the prostate cavity. In this manner, efficient flush irrigating of the prostate is achieved, while retaining effective drainage of the bladder. Separate drain bags (not shown) can be connected to urine drain ports 70 and to fluid drain ports 74 to keep discharge from the prostate separate from that of the bladder. This separate drainage allows the attending physician to assess and monitor the two organs independently.

Figure 5:
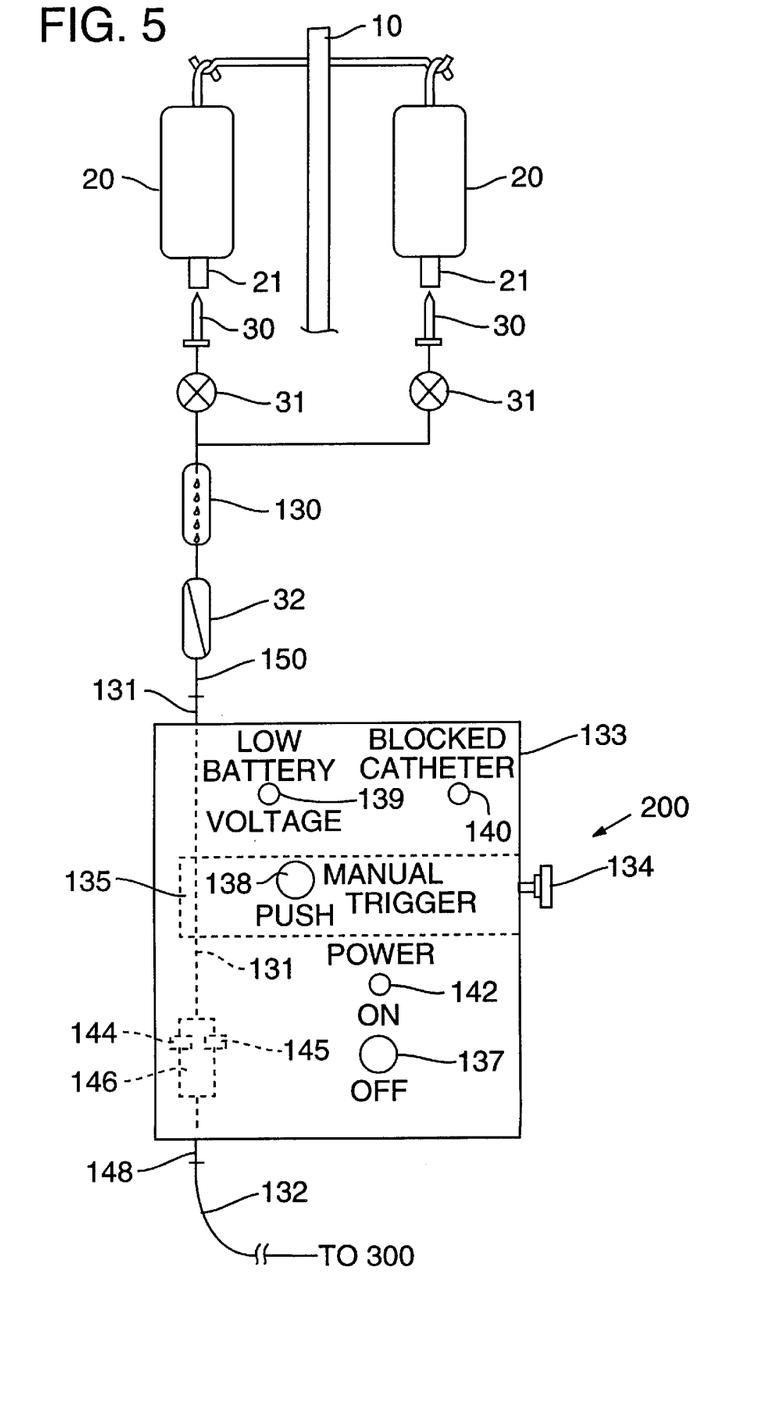
FIG. 5 is a schematic view in elevation of the alternative embodiment of the invention when assembled with the irrigant supply components to form a complete catheterization system.

FIG. 5 is a schematic diagram of an alternative embodiment of the electronic control unit of the invention, ECU 200, shown in its operating environment. ECU 200 is used only when constant urinary irrigation is indicated. While the preferred embodiment of the electronic control unit, ECU 170, automatically resumes the selected irrigant flow mode should a catheter obstruction subsequently be cleared, the alternate embodiment, ECU 200, is a lower-cost, manually-operated unit that must be set and reset by hand. When ECU 200 detects a blocked catheter, it interrupts the flow of irrigant and sets off an alarm, as in the preferred embodiment. Unlike the preferred embodiment, ECU 200 does not automatically resume the flow of irrigant after the obstruction is cleared. Instead, ECU 200 must be reset manually before the flow of irrigant will resume.

Referring to FIG. 5, supply bags 20 are suspended from conventional IV pole 10, and hollow spikes 30 are driven into sealed outlets 21. Irrigant then flows from supply bags 20 under the force of gravity through on/off valves 31 and to sight gauge 130 and flow regulating clamp 32, which allow the user to regulate the flow (drip) rate of the irrigant by observing the drip rate in sight gauge 130. The irrigant then flows into tubing segment 150, which connects to resilient thin-walled tubing section 131, as described further below in connection with FIG. 6A. Irrigant enters ECU 200 and pinch valve 135 via tubing section 131 and exits blocked catheter detector 146 via tubing section 132, which joins to ECU 200 via fitting 148. Tubing section 132 carries the irrigant to the irrigating lumen of the patient's catheter, which is not illustrated in FIG. 5.

ECU 200 is housed within cabinet 133, which may be formed from any suitable rigid material in any convenient shape. ECU 200 is preferably powered by a 9-volt alkaline battery. Mounted exteriorly of cabinet 133 are LEDs 139 and 140, which indicate low battery voltage and blocked catheter conditions, respectively. Switch 137 controls the power supply to cabinet 133, and LED 142 indicates power-on.

Figure 6:
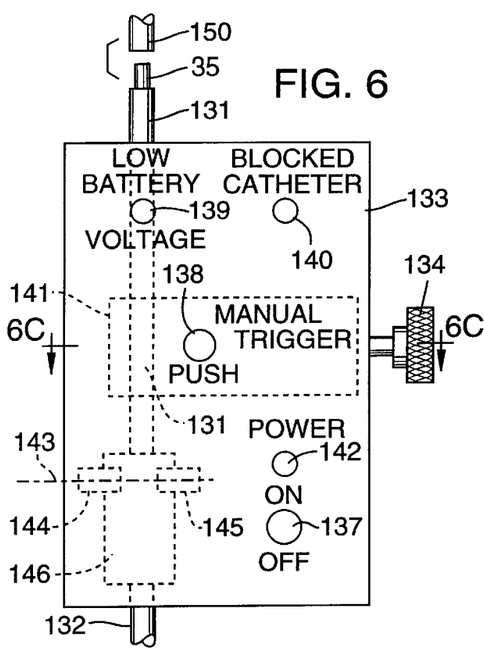
FIG. 6 is a detailed schematic view of the control unit used in the alternative embodiment.
Figure 6A:
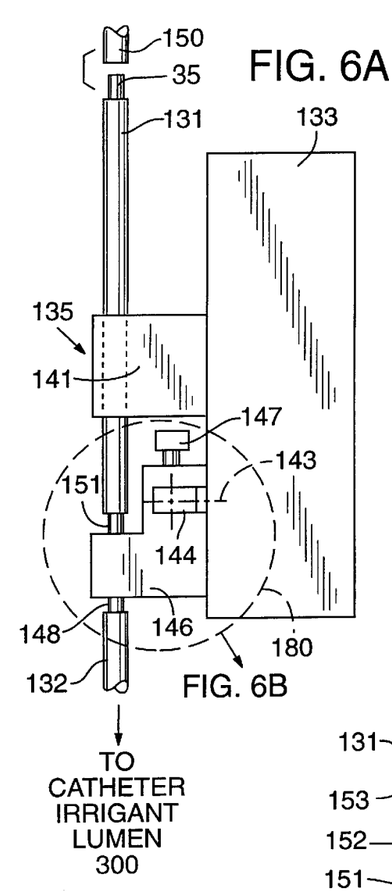
FIG. 6A is a side view of the alternative embodiment as shown in FIG. 6.
Figure 6B:
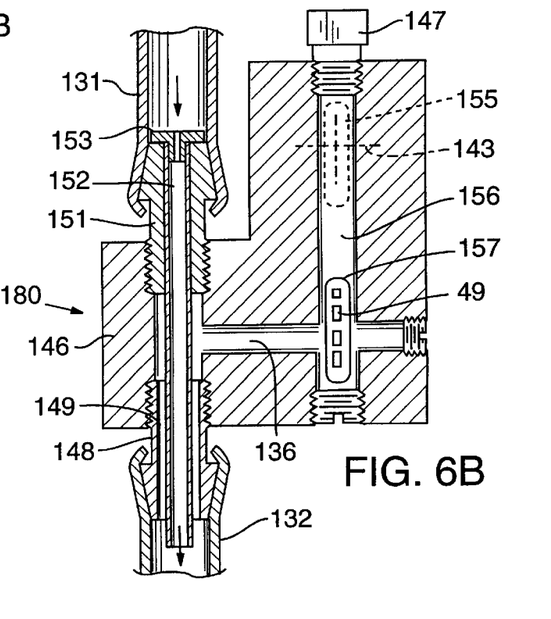
FIG. 6B is a fragmentary, detailed, sectional view of the blocked catheter detector and fluid sensor assembly for the alternative embodiment as shown in FIG. 6.
Figure 6C:
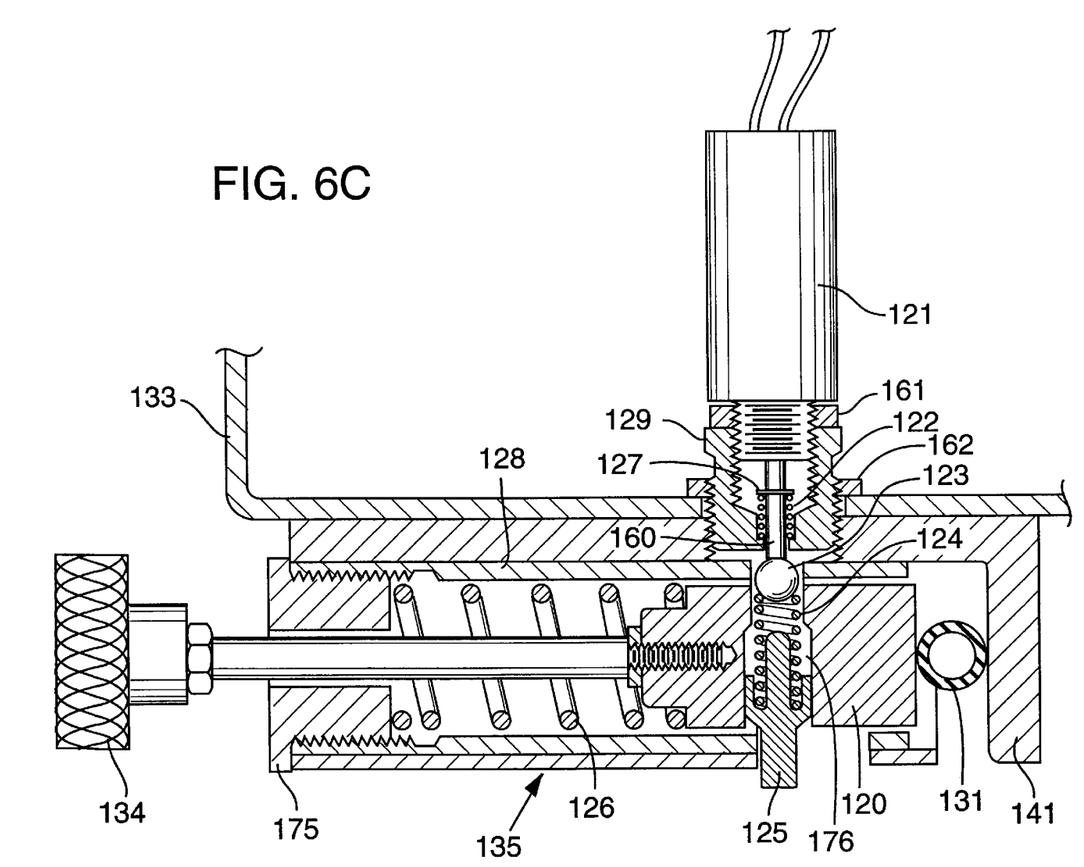
FIG. 6C is a fragmentary, detailed, sectional view of the manually cocked solenoid-actuated pinch-valve and trigger assembly of the alternative embodiment, taken along the line 6C—6C in FIG. 6.

Per FIG. 6C, pinch valve assembly 135, attaches to cabinet 133. In its closed position, pinch valve plunger 120 firmly contacts tubing segment 131, pinching it shut and interrupting the flow of irrigant to the patient's catheter. In its open position, pinch valve plunger 120 is spaced from tubing segment 131, and allows irrigant to flow freely through tubing segment 131 and on to the patient's catheter. Pinch valve assembly 135 is cocked open by manually pulling knob 134 outwards into a locked, extended position. In this position, pinch valve assembly 135 is said to be cocked. With pinch valve assembly 135 open and cocked, tubing section 131 is slid into position within pinch valve 135. The precise positioning of tubing section 131 will be described further below in connection with FIGS. 6A and 6B.

Once pinch valve assembly 135 is cocked in its open position, it can be released one of two ways. First, if ECU 200 detects a blocked catheter, it will close pinch valve assembly 135 automatically to terminate the flow of irrigant. Second, the user can manually terminate the flow of irrigant by pressing button 138, which is operatively joined to a release mechanism that closes pinch valve plunger 120.

Mounted exteriorly of cabinet 133 is fluid sensor assembly 180, shown in dashed outline in FIG. 5. Fluid sensor assembly 146 includes means 144 and 145 for generating a control circuit indicating the status of the patient's catheter. The control circuit is operable in at least two states. The first state indicates that the patient's catheter is clear and functioning normally. When the control circuit is in the first state, ECU 200 allows irrigant to flow to patient's catheter by maintaining pinch valve assembly 135 open. The second state indicates that the patient's catheter is obstructed, and needs immediate attention. When the control circuit is in the second state, ECU 200 terminates the flow of irrigant by closing pinch valve assembly 135.

Clearly, the control circuit can be implemented a number of different ways, such as defining a circuit having a normally-open first state, and transitioning to a closed second state that indicates a catheter obstruction. Alternatively, the circuit could be defined with a normally-closed first state, and transitioning to an open second state.

As in the preferred embodiment, the preferred means 144 and 145 for generating a control circuit are a photon emitter and a photon detector defining a normally-closed circuit that is opened by an opaque float. However, depending upon the application, other components for generating a selectively interruptible control circuit may be suitable. Although the operative medium in the preferred embodiment is photon energy, other electrical media may suitable, such as electronic signals, electromagnetic fields, direct current connections, or digital signals. Also, mechanical devices such as microswitches or other mechanical switchgear may be suitable in some applications.

FIG. 6 is a more detailed schematic diagram of ECU 200. FIG. 6A is a side elevational view of ECU 200, as shown in FIG. 6. Tubing 150 connects to pliable thin-walled tubing 131 via a short piece of rigid tubing 35, which has an outer diameter that is about the same as the inner diameter of tubing 150 and 131. Other adapting means providing for liquid-tight connections between two pieces of flexible tubing may be appropriate in certain applications. Tubing 131 extends into pinch valve assembly 135 and then to fluid sensor assembly 180. After passing through fluid sensor assembly 180, tubing 131 connects to tubing 132, and passes on to the patient's catheter (not shown).

FIG. 6B is a detailed schematic view of fluid sensor assembly 180. Fluid sensor assembly 180 includes housing 146. Incoming tube 131 connects to housing 146 by fitting 151. Connector tube 152 is fitted internally of housing 146, and places incoming tubing 131 in direct fluid communication with outgoing tube 132. Flow restrictor 153 is joined to the upstream side of fitting 151, and promotes the slow, steady flow of irrigant into connector tube 152. Housing 146 also defines annulus 149, which is in fluid communication with both incoming tube 131 and outgoing tube 132. Housing 146 also defines connecting cavity 136, which is in fluid communication with annulus 149. Finally, housing 146 defines a cavity 156, which is in fluid communication with connecting cavity 136. Connecting cavity 136 is positioned above the discharge outlet of connector tube 152 discharging into outgoing tube 132, thereby assuring that no fluid will enter annulus 149, connecting cavity 136, and cavity 156, unless the flow of fluid in outgoing tube 132 is restricted by a catheter obstruction. This design prevents ram 120 from being triggered closed due to false alarms.

Slidably positionable within cavity 156 is manipulating means 157. Preferably, manipulating means 157 includes an opaque float, which is biased by gravity into its rest position as shown in FIG. 6B. Opaque in this context means being sufficiently translucent to block photons from flowing between the photon emitter and the photon detector, as in the preferred embodiment. Thus, the definition of "opaque" will vary depending on which photon emitter and photon detector is chosen. Hydrophobic vent 147 is mounted on housing 146 in fluid communication with cavity 156, and prevents cavity 156 from becoming "air-locked" when it fills with irrigant, as explained below. Cavity 156 is preferably vertically-disposed, allowing gravity to bias manipulating means 157 into a downward position. Manipulating means 155, shown in dashed outline, is manipulating means 157 in its raised floating position.

Manipulating means 157 should be chosen to interact with the control circuit generated by means 144 and 145. As stated above, means 144 and 145 can generate a control circuit having a number of configurations and using several different operative media. The choice of manipulating means 157 will vary depending on the choice of control circuit configuration and operative media. For example, if the control circuit is chosen as a normally-open circuit transitioning to a closed state when the catheter is obstructed, then manipulating means 157 should be chosen to make the control circuit when fluid sensor assembly 180 indicates that the catheter is obstructed.

Fluid sensor assembly 180 operates as follows. Irrigant enters fluid sensor assembly 146 via incoming tube 131, and passes through flow restrictor 153 into connector tube 152. The irrigant then passes through connector tube 152, discharging into outgoing tube 132 and thence to the patient's catheter (not shown). However, should the catheter become obstructed, then pressure will build within outgoing tube 132, causing irrigant to flow back into annulus 149. Annulus 149 directs the back-flowing irrigant into connecting cavity 136, and then into cavity 156. As cavity 156 fills with irrigant, manipulating means 157 is lifted from its rest position, and is eventually raised into position 155 shown in dashed outline in FIG. 6B. As cavity 156 fills with irrigant, the ambient air within cavity 156 is forced upwards and out through hydrophobic vent 147. When manipulating means 157 is in its raised position, it interacts with the control circuit generated by means 144 and 145. This interaction between manipulating means 157 and generating means 144 and 145 notifies ECU 200 that the patient's catheter has become obstructed and needs immediate attention and shuts off any further irrigant flow. ECU 200 then closes pinch valve assembly 135, as described below in connection with FIG. 6C, lights LED 140, and sounds an audible buzzer and/or alarm (not shown) to alert nursing personnel. After the catheter is cleared and the irrigant recedes from cavity 156, manipulating means 157 returns to its downward rest position, returning the control circuit to its original state. At this point, ECU 200 is then ready to be manually re-cocked to resume the flow of irrigant.

FIG. 6C is a schematic diagram of pinch valve assembly 135, as viewed from above. Tubing 131 passes between anvil 141 and ram 120. Tubing 131 is preferably a thin-walled, flexible tubing made from a resilient material such as silicon. Tubing 131 should be readily compressible, yet be rugged enough not to tear when contacted firmly by ram 120, and be resilient enough to rebound readily to its original, uncompressed cross-section even after extended periods of compression. Ram 120 is reciprocally mounted within cylinder 128 attached to housing 141. Ram 120 is slidable between two positions, a closed position wherein tubing 131 is compressed and pinched-off against the anvil portion of housing 141, and an open position wherein tubing 131 remains partially uncompressed. When ram 120 is in the closed position, irrigant flow through tubing 131 is interrupted, and when ram 120 is in the open position, irrigant flows freely through tubing 131, unless an obstructed catheter condition is detected.

Ram 120 is urged toward anvil 141 by spring 126, which is rigidly seated against spring seat 175. However, ram 120 also defines a radial cavity 176, which carries a hardened steel check ball 123. Check ball 123 is biased away from the central axis of ram 120 by spring 124, which is seated against spring seat 125, which is located in a slot in housing 141, thereby preventing spring seat 125 and check ball 123 from rotating within cylinder 128.

"Push" solenoid 121 is mounted perpendicularly to the path traveled by ram 120. Plunger 160, driven by solenoid 121, contacts check ball 123. When solenoid 121 is not activated, check ball 123 is held in position between ram 120 and cylinder 128 so that check ball 123 holds ram 120 in place against the force exerted by spring 126, thereby holding ram 120 in its open position. Typically, check ball 123 is held slightly off-center relative to ram 120 and cylinder 128. The precise position of check ball 123 relative to ram 120 may be adjusted via bushing 129, which threads into housing 141 and threadably receives the base of solenoid 121. Once properly positioned, solenoid 121 and bushing 129 are locked in place by jamb nuts 161 and 162. Thus, the position of solenoid 121, and indirectly the rest position of plunger 160, can be adjusted by threading or unthreading bushing 129. This adjustment can be done at the factory or on-site.

When solenoid 121 is activated, plunger 60 pushes check ball 123 into cavity 176 against the force of spring 124. As soon as check ball 123 clears cylinder 128 and enters cavity 176, ram 120 is released, and spring 126 drives ram 120 toward anvil 141, pinching tubing 131 therebetween, and interrupting the flow of irrigant in tubing 131. Solenoid 121 is preferably activated with only a short electrical pulse, which drives plunger 160 only momentarily. After that short pulse, spring 122, which is seated against bushing 129 and which engages snap ring 127 of plunger 160, drives plunger 160 toward solenoid 121 and out of the way of the advancing ram 120.

Because solenoid 121 is normally deactivated, and only requires a short pulse of power when it is activated, solenoid 121 can be powered by a conventional 9-volt alkaline battery. This minimal power requirement not only promotes patient safety, but also makes ECU 200, eliminating its reliance on AC power. This design also reduces the expense of producing ECU 200.

Once ram 120 has pinched-off tubing 131, ram 120 remains in its closed position until it is manually reset by pulling knob 134. As ram 120 is withdrawn toward its rest position, spring 124 urges check ball 123 into an "over the center" relationship between the sliding surfaces of cylinder 128 and plunger 120. When ram 120 reaches its rest position, spring 124 drives check ball 123 into engagement with plunger 160, locking ram 120 into position, and re-opening tubing 131 to the flow of irrigant.

This style of ECU would, ideally, be used in conjunction with the 3-way irrigating catheter inasmuch as this type of catheter is generally used where CBI (Constant Bladder irrigation) is indicated, and its primary purpose would be to detect a blocked catheter condition and shut off any further flow of irrigant until the catheter is cleared and the pinch valve manually cocked to again open the valve and resume flow.

Inasmuch as this embodiment is ideally suited to the use of constant bladder irrigation, the tubing assembly would differ from that used in the previously described preferred embodiment. This assembly could either be a custom-designed one for use with this second embodiment electronic control unit, or it could make use of the existing style of tubing assembly currently in use with the 3-way catheter by cutting the original tubing at the junction of 150-132 and inserting the special thin-walled flexible section of the tubing assembly 131 using connectors 35 and 148. Tubing 131 and connectors 35 and 148 would be supplied in a pre-sterilized package in order to maintain the sterility of the original tubing assembly. Both methods will be described in more detail under the OPERATION section of this application.

OPERATION

The operation of the above described urinary tract treating assembly for the preferred embodiment is as follows:

After hanging irrigation fluid bag(s) 20 on pole 10, the operator connects the bag(s) 20 to the tubing assembly by means of puncturing sealed outlet(s) 21 with hollow spike(s) 30. On/off valve(s) 31 are used to connect either or both bags to the pre-packaged, pre-sterilized tubing assembly as desired.

Flexible segment 35 of the conduit is positioned in recess 92 of bracket 90 after retracting spring-loaded ram plunger 94. Ram 94 is designed to be operated either manually by means of lever 96, or electronically by means of manual electric switch 104.

The collapsible bag(s) 20 discharges fluid into a regulating clamp 32 which is used to regulate the rate of flow of irrigant as it refills reservoir 34 between flushes. Generally this flow rate would be such that it would require approximately 3 minutes to refill reservoir 34, unless a continuous flow rate into the catheter is desired, in which event regulating clamp 32 would be adjusted to the desired flow rate, and reservoir 34 would be used as a drip chamber in order to visually adjust the desired flow rate.

Upon filling reservoir 34, and the desired time interval has elapsed, pinch valve 88 is actuated either manually or electronically. Thereupon the charge of fluid flows through flow restrictor 37 and discharges out tube 38 into sump reservoir 39, through tubing 40 and thence into the irrigating lumen of catheter 300 thereby irrigating the desired urinary organ through either ports 64 or 73, depending on which organ (bladder or prostate) is to be irrigated and which catheter type (3-way or 4-way) is selected. The spent irrigation fluid exits via appropriate drain ports 63 or 74 where it is collected in a drain bag (not depicted) provided for that organ. When conventional 3-way catheter is used, drain ports 63 will drain the contents of the bladder (urine and/or spent irrigant) and only one bag is provided for this collection. When a 4-way catheter is used, however, two separate bags are used to separately collect the contents of both the bladder and the prostate by means of drain ports 70 and 74, respectively, thereby allowing the attending physician to assess each organ separately by viewing the discharge collected in the separate bags.

The above described assembly may thus be operated automatically over long operating periods. In the event of an inadvertent malfunction, such as one caused by clot-blockage of the catheter, or kinking of the tubing 40, aqueous sensitive detector switch 110 will terminate the flow of irrigant; thus patient comfort and safety are assured.

The operation of the second embodiment of this invention is as follows:

Irrigation bag(s) 20 are hung on pole 10 as before and hollow spikes 30 are punctured into sealed tubing 21, Ram 120 is retracted by pulling on knob 134 (FIG. 6C) to cock the device and flexible conduit 131 is inserted between ram 120 and body 141. Tubing 132 is connected to the irrigating lumen of catheter 300 (not shown) in preparation for urinary irrigation.

Sight gauge 130 is used to visually determine the rate of flow as controlled by regulating valve 32, and on/off valve(s) 31 are opened as desired to initiate flow from bag(s) 20.

Fluid would flow through restrictor 153, through tubing 152 and discharge into tubing 132 and thence into the irrigating lumen of catheter 300. In the event the catheter drain(s) become blocked, or tubing 132 is inadvertently kinked, the irrigating fluid would back up into annulus 149 of fitting 146 and then into float cavity 156, resulting in opaque float 157 departing from its normal lower position to optically block the photo-coupled interrupter module 144-145 emitter and detectors, thereby actuating push solenoid 121. Solenoid plunger 160 is normally held retracted by spring 122.

During factory assembly, bushing 129 depth is adjusted in such a manner that in the "cocked" mode, the hardened steel ball 123 positioned between relative sliding surfaces of ram 120 and cylinder 128 is in a slightly "over the center" position sufficient to hold the ram in its cocked condition despite the urging of spring 126 to close the ram against tubing 131. Upon actuating "push" solenoid 121 with a single short electrical pulse, solenoid plunger 160 strikes the ball 123 with sufficient force to dislodge the ball from its cocked position, permitting spring 126 to slam the ram against the tubing 131, thereby shutting off the further flow of fluid. Simultaneously it turns on a flashing LED 140 and an audible buzzer (not depicted) to alert the patient and/or medical personnel that a catheter blockage has occurred.

Inasmuch as power to the solenoid would be limited to a few milliseconds sufficient to dislodge ball 123, this device could be powered by a 9 volt alkaline battery. A low battery voltage indicator LED 139 would be provided to advise of this condition should it occur.

The tubing assembly used with this embodiment could either be a custom designed assembly as depicted in FIG. 5, or it could be adapted by furnishing only tubing 131 together with blocked catheter detector unit 180 as a disposable pre-sterilized unit that would be inserted between tubing 150 and 132 after separating these in the field.

Having thus described in detail a preferred embodiment as well as a second embodiment of the present invention, it will be apparent to those skilled in the art that many physical changes may be made without altering the inventive concepts and principles embodied therein. The present embodiment therefore are to be considered in all respects as illustrative and not restrictive, the scope of the invention being indicated by the appended claims:

It should be understood that the above description is made only by way of example, and is not intended to limit the scope of the invention. Certain modifications may be made to the invention without departing from the spirit of the invention, which is defined by the appended claims.

I claim:

1. An electronic control unit for automatically interrupting the flow of irrigant to a urinary catheter, the control unit being connectable to a fluid sensor for automatically detecting an obstruction of a catheter, the control unit comprising:
    a) means for generating a control circuit being responsive to the fluid sensor, the control circuit being operable in at least two states, a first one of the at least two states indicating that there is no obstruction, and a second one of the at least two states indicating that there is an obstruction;
    b) means for selectively interrupting the flow of irrigant, said interrupting means being responsive to the control circuit so that when the control circuit is in the first state, said interrupting means allows irrigant to flow and so that when the control circuit is in the second state, said interrupting means blocks the flow of irrigant;
    c) said generating means including means for emitting a control signal and means for detecting the control signal; and
    d) said emitting means including a photon emitter, and said detecting means including a photon detector.

2. The control unit of claim 1, wherein said interrupting means includes a pinch valve assembly being movable between an open and a closed position.

3. The control unit of claim 2, wherein said pinch valve assembly includes a solenoid being responsive to the control circuit, and a ram being joined to said solenoid, said ram for selectively contacting the supply line.

4. A tubing apparatus for use with an irrigating urinary catheter having an irrigant supply line fed by an irrigant source and at least one drain lumen, the tubing apparatus being connectable to a control unit generating a control signal, the tubing apparatus being configured to automatically detect when the drain lumen or the supply line of a catheter becomes obstructed, and for manipulating the control signal to indicate the presence of an obstruction in a catheter, the tubing apparatus comprising:
    a) a vent line being arranged so that irrigant flows into said vent line only should an obstruction occur; and
    b) a fluid sensor being in fluid communication with said vent line for detecting irrigant within said vent line, said fluid sensor being connectable to the control unit in communication with the control signal, so that said fluid sensor automatically detects obstructions and manipulates the control signal when obstructions are detected.

5. The tubing apparatus of claim 4, wherein said vent line includes an elongated hollow lumen.

6. The tubing apparatus of claim 4, further comprising a junction member being joined to said vent line, the irrigant source, and to a supply line.

7. The tubing apparatus of claim 6, wherein said junction member includes a housing, and wherein said housing defines an interior channel being in fluid communication with the irrigant supply line, the irrigant source, and said vent line.

8. The tubing apparatus of claim 7, wherein the interior channel is generally T-shaped.

9. The tubing apparatus of claim 4, wherein said fluid sensor includes means for manipulating the control circuit, said manipulating means being in fluid communication with said vent line and being responsive to the presence of irrigant within said vent line.

10. The tubing apparatus of claim 9, wherein said manipulating means includes a float.

11. The tubing apparatus of claim 4, wherein said fluid sensor defines an internal cavity being in fluid communication with said vent line, and wherein said fluid sensor includes a float being slidably positionable within the internal cavity between a resting position, wherein the float allows the control signal to pass unmanipulated, and a floating position, wherein the float manipulates the control signal.

12. The tubing apparatus of claim 11, wherein said float includes an exterior surface area and a plurality of knobs protruding from the external surface area, the knobs being for minimizing the area of contact between the external surface area of the float and the wall of the internal cavity.

13. The tubing apparatus of claim 11, wherein the internal cavity is oriented so that gravity biases the float into the resting position, and so that irrigant passing into the internal cavity from said vent line raises the float into the floating position.

14. A system for use with a urinary irrigating catheter having an irrigant supply line and at least one drain lumen, the system being configured to automatically interrupt the flow of irrigant should the drain lumen or the supply line of the catheter become obstructed, and for automatically resuming the flow of irrigant should an obstruction subsequently be cleared from the catheter, the system comprising:
   a) a control unit comprising:
      i) means for generating a control circuit indicating when an obstruction occurs, the control circuit being operable in at least two states, a first one of the at least two states indicating that no obstruction is present, and a second one of the at least two states indicating that an obstruction is present; and
      ii) means for selectively interrupting the flow of irrigant, said interrupting means being responsive to the control circuit so that when the control circuit is in the first state, said interrupting means allows irrigant to flow, and so that when the control circuit is in the second state, said interrupting means blocks the flow of irrigant; and
   b) a tubing apparatus comprising:
      i) a vent line being in fluid communication with the irrigant supply line so that irrigant flows into said vent line only should an obstruction be present; and
      ii) a fluid sensor being in fluid communication with said vent line for detecting irrigant within said vent line, said fluid sensor being connectable to said generating means in communication with the control circuit, so that said fluid sensor alters the state of the control circuit when an obstruction is present.

15. The system of claim 14, wherein said fluid sensor includes means for manipulating the control circuit, said manipulating means being in fluid communication with said vent line and being responsive to the presence of irrigant within said vent line.

16. The system of claim 15, wherein said manipulating means includes a float.

17. The system of claim 14, wherein said fluid sensor defines an internal cavity being in fluid communication with said vent line, and wherein said fluid sensor includes a float being slidably positionable within the internal cavity between a resting position, wherein the float allows the control signal to pass unmanipulated, and a floating position, wherein the float manipulates the control signal.

18. The system of claim 14, wherein said interrupting means includes a pinch valve assembly being movable between an open and a closed position.

19. The system of claim 14, wherein said generating means includes means for emitting a control signal and means for detecting the control signal.

20. The system of claim 19, wherein the emitting means includes a photon emitter, wherein the detecting means includes a photon detector, wherein the float is opaque, whereby the opaque float blocks photons passing between the emitter and the detector when the float is in the floating position to manipulate the control circuit.

21. An electro-mechanical control unit for automatically interrupting the flow of irrigant to a urinary catheter should the catheter become obstructed, the electro-mechanical control unit comprising:
   a) means for generating a control circuit, the control circuit being operable in at least two states, the first state indicating no obstruction, and the second state indicating the presence of an obstruction;
   b) means for manipulating the state of the control circuit to indicate the presence of an obstruction;
   c) a housing defining an annulus being in communication with said manipulating means, the annulus being arranged so that it fills with irrigant should an obstruction occur and so that the irrigant causes said manipulating means to alter the state of the control circuit; and
   d) means for selectively interrupting the flow of irrigant, said interrupting means being responsive to the control circuit so that when the control circuit is in the first state, said interrupting means allows irrigant to flow, and so that when the control circuit is in the second state, said interrupting means blocks the flow of irrigant.

22. The electro-mechanical control unit of claim 21, wherein said generating means includes a photon emitter and a photon detector generating the control circuit.

23. The electro-mechanical control circuit of claim 21, wherein said manipulating means includes a float.

24. The electro-mechanical control of claim 23, wherein said housing defines a cavity, and the float is slidably positioned within the cavity.

25. The electro-mechanical control unit of claim 24, wherein the cavity is disposed so that the float is biased by gravity downwardly within the cavity.

26. The electro-mechanical control unit of claim 23, wherein the float is opaque.

27. The electro-mechanical control unit of claim 21, wherein said interrupting means includes a manual ram being movable between an open and a closed position.

28. An electronic control unit for periodically flushing a urinary irrigating catheter with irrigant while providing a plurality of modes, the electronic control unit comprising:
   (a) means for selectively interrupting the flow of irrigant to the catheter, said interrupting means being movable between an open position allowing the flow of irrigant and a closed position blocking the flow of irrigant; and
   (b) means for selecting the flush mode, said selecting means being operatively connected to said interrupting means periodically to open said interrupting means to flush the catheter with irrigant.

29. The electronic control unit of claim 28, wherein said selecting means includes means for allowing a user to select a one-shot flushing mode.

30. The electronic control unit of claim 28, wherein said selecting means includes means for allowing a user to select a continuous flow mode.

31. The electronic control unit of claim 28, wherein said selecting means includes means for allowing a user to select an automatic flow mode wherein a measured volume of irrigant is released according to a selected periodic time schedule.

32. The electronic control unit of claim 28, further comprising means for controlling the volume of irrigant flushed, said controlling means being operatively connected to said interrupting means.

* * * * *